United States Patent [19]

Guittard et al.

[11] Patent Number: 5,178,867
[45] Date of Patent: * Jan. 12, 1993

[54] DOSAGE FORM FOR DELIVERING DRUG IN SHORT-TIME PERIOD

[75] Inventors: George V. Guittard, Cupertino; Howard A. Carpenter, Palo Alto; Ernest S. Quan, Fremont; Patrick S. Wong, Palo Alto; Lawrence G. Hamel, Sunnyvale, all of Calif.

[73] Assignee: Alza Corporation, Palo Alto, Calif.

[ * ] Notice: The portion of the term of this patent subsequent to Aug. 14, 2007 has been disclaimed.

[21] Appl. No.: 747,899

[22] Filed: Aug. 19, 1991

[51] Int. Cl.$^5$ ............................................. A61K 9/22
[52] U.S. Cl. ...................................... 424/473; 424/468
[58] Field of Search ........................................ 424/473

[56] References Cited

U.S. PATENT DOCUMENTS

| 2,799,241 | 7/1957 | Wurster | 118/24 |
|---|---|---|---|
| 3,845,770 | 11/1974 | Theeuwes et al. | 128/260 |
| 3,916,899 | 11/1975 | Theeuwes et al. | 128/260 |
| 4,063,064 | 12/1977 | Saunders et al. | 219/121 |
| 4,077,407 | 3/1978 | Theeuwes et al. | 128/260 |
| 4,088,864 | 5/1978 | Theeuwes et al. | 219/121 |
| 4,160,020 | 7/1979 | Ayer et al. | 424/15 |
| 4,200,098 | 4/1980 | Ayer et al. | 128/260 |
| 4,285,987 | 8/1981 | Ayer et al. | 427/3 |
| 4,327,725 | 4/1982 | Cortese et al. | 128/260 |
| 4,576,604 | 3/1986 | Guittard et al. | 604/890 |
| 4,612,008 | 9/1986 | Wong et al. | 604/892 |
| 4,783,337 | 11/1988 | Wong et al. | 424/468 |
| 4,801,461 | 1/1989 | Hamel et al. | 424/467 |
| 4,948,592 | 8/1990 | Ayer et al. | 424/473 |

Primary Examiner—Thurman K. Page
Assistant Examiner—Raj Bawa
Attorney, Agent, or Firm—Paul L. Sabatine; Jacqueline S. Larson; Jean M. Duvall

[57] ABSTRACT

The invention pertains to a dosage form for orally administering a drug in eight hours or less to the stomach and small intestine for a therapeutic result.

24 Claims, 1 Drawing Sheet

DOSAGE FORM FOR DELIVERING DRUG IN SHORT-TIME PERIOD

FIELD OF THE INVENTION

This invention pertains to (1) a novel dosage form for administering a drug in a time period up to eight hours. More specifically, the invention concerns (2) a dosage form for orally administering a drug for absorption in the stomach and for absorption in the small intestine in a period up to eight hours. The invention relates also to (3) the use of a dosage form in a method for administering a drug for a therapeutic effect and to (4) a process for providing a dosage form for delivering a drug in a period of time comprising immediately and then up to eight hours.

DESCRIPTION OF BACKGROUND ART

Oral ingestion is the most common method of drug administration. Oral ingestion is the safest, the most convenient and the most economical form of drug administration. Furthermore, because oral ingestion comprises administering dosage forms such as tablets and capsules that are relatively small, and because drug absorption often is rapidly completed, drug absorption is limited usually to the stomach and to the small intestine. The small intestine is the primary site from which orally administered drugs are absorbed, and few drugs are absorbed in any significant dose from the stomach.

There are several biological reasons for the small intestine serving as the primary site for drug absorption. For example, the small intestine has an absorptive area about two-hundred times greater than the absorptive area of the stomach for increasing the dose of drug absorbed per unit time. In addition, the intestinal epithelium is more permeable to the passage of drug than is the mucosal lining of the stomach permeable to the passage of drug, thereby increasing the absorptive ability of the intestine. Moreover, the quantity of blood flow through the intestinal capillaries is greater than in the stomach, which leads to more drug being admitted into the systemic circulation from the intestine. Generally, the intestine is designed from drug absorption, while the stomach can be considered a reservoir where drug is released in increments to the small intestine for absorption therein. The drug absorption properties of the stomach and the intestine are presented in the following references: *The Pharmacological Basis of Therapeutics*, by Goodman and Gilman, 8th Ed., pages 6 and 7, (1990); *Drug Interactions Newsletter*, by Hansten and Horn, Vol. 9, pages 475 to 480, (1989); and, *Novel Drug Delivery And Its Therapeutic Application*, by Prescott and Nimmo, Ch. 8, pages 79 to 88, and Ch. 9, pages 89 to 101, (1989).

The prior art administered drugs orally using non-controlled dosage forms that delivered a drug throughout the entire gastrointestinal tract consisting of the stomach, small intestine, large intestine and the rectal vault. While the prior art possessed the ability to deliver a drug throughout the entire gastrointestinal tract, the prior art lacked the precision required for delivering a drug only to the stomach and only to the primary site of absorption, the small intestine. The prior art delivered drug from the stomach to the rectal vault results in the administration of unneeded drug, which can be accompanied often by unwanted side effects.

It is self evident from the above presentation to those versed in the dispensing drug art to which this invention pertains that a pressing need exits for a rate controlled dosage form that can deliver a valuable drug to a preselected absorption site of the gastrointestinal tract. This pressing need exists for an oral dosage form that can deliver a drug to the preferred sites of absorption at a controlled rate in a constant dose per unit time over a selected period of time. The need exists for such a dosage form that delivers a drug for its therapeutic effect substantially independent of the variable environment of the gastrointestinal tract. It will be appreciated further by those versed in the dispensing art, that such a novel and unique dosage form that can administer a drug to a preselected area of the gastrointestinal tract in a rate controlled dose over time, and simultaneously provide for the desired site-specific therapy, such a dosage form would represent an advancement and a valuable contribution to the drug delivery art.

DESCRIPTION OF OBJECTS OF THE INVENTION

Accordingly, in view of the above presentation, it is an immediate object of this invention to provide a dosage form for delivering a drug in a rate-controlled dose, and which dosage form substantially overcomes the deficiencies associated with the prior art.

Another object of the invention is to provide a novel dosage form for administering a therapeutically effective drug in a short time period up to eight hours for producing a preselected therapeutic effect.

Another object of the present invention is to provide a dosage form for administering a therapeutically effective drug immediately from the external surface of the dosage form followed by administering a therapeutically effective dose of drug from inside the dosage form from ten minutes up to eight hours for producing a preselected therapeutic effect.

Another object of the invention is to provide a novel dosage form for orally administering a drug at a rate-controlled dose to the stomach and to the small intestine for the management of health and disease.

Another object of the invention is to provide a dosage form manufactured as an osmotic device that can administer a drug to a biological receptor site selected from the group consisting of stomach and small intestine sites to produce a desired pharmaceutically-acceptable effect.

Another object of the present invention is to provide a dosage form manufactured as an osmotic dosage form that substantially reduces and/or substantially eliminates the unwanted influences of the gastrointestinal environment of use and still provides controlled drug administration to the stomach and to the small intestine over time.

Another object of the invention is to provide a dosage form useful in a method for administering a histamine $H_2$ receptor antagonist that inhibits both daytime and nocturnal basal gastric acid secretion.

Another object of the present invention to provide a dosage form for orally administering a drug to the small intestine, which small intestine comprises the duodenum, the jejunum and the ileum for drug absorption into the blood circulation system for producing a therapeutic effect in a patient in need of therapy.

Another object of the invention is to provide a dosage form that delivers a drug from the external surface of the dosage form and delivers a drug through the exit port from inside the dosage form to the duodenum, the jejunum and to the ileum.

Another object of the present invention is to provide a dosage form manufactured as an osmotic dosage form comprising an improvement for delivering a maximum dose of drug over a short time of up to eight hours.

Another object of the present invention is to provide an osmotic dosage form comprising an increased fluid flux into the dosage form for enabling the dosage form to osmotically pump a dose of drug in a short time of greater than twenty minutes up to eight hours.

Another object of the invention is to provide a complete pharmaceutical regimen comprising a drug composition administrable to the stomach and the small intestine from a drug delivery device, the use of which device requires intervention only for initiation and possibly for termination of the regimen.

Another object of the invention is to provide the use of a dosage form in a method for treating a disease or a condition by orally administering the dosage form for delivering in a rate controlled dose a drug for treating the disease or the condition.

Another object of the invention is to provide a dosage form useful in a method for administering an inhibitor of angiotensin converting enzyme activity.

Another object of the invention is to provide a dosage form useful for delivering a drug that is a competitively reversible inhibitor of histamine at the histamine $H_2$ receptors, particularly those in the gastric parietal cells.

Another object of the invention is to provide a dosage form useful in a method for administering a calcium ion influx inhibitor that inhibits the transmembrane influx of calcium ions into cardiac muscles and smooth muscles.

Other objects, features and advantages of the invention will be more apparent to those versed in the dispensing arts from the following detailed specification taken in conjunction with the drawings and the accompanying claims.

BRIEF DESCRIPTION OF THE DRAWINGS

In the drawing figures, which are not drawn to scale, but are set forth to illustrate various embodiments of the invention, the drawing figures are as follows.

In the drawing figures and in the specification, like parts in related drawing figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 1:
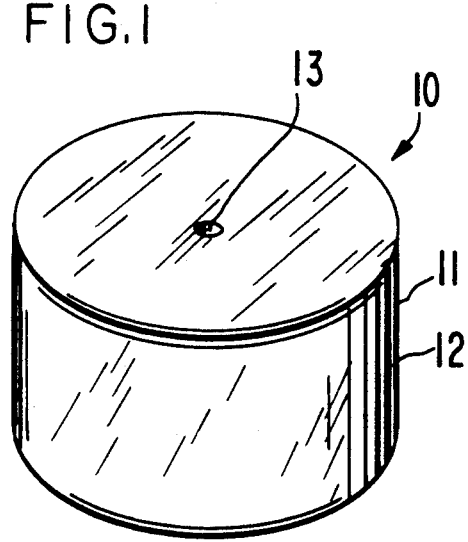
FIG. 1 is a general view of a dosage form provided by the invention, which dosage form is designed and shaped for oral administration for delivering a drug to a preselected section of the gastrointestinal tract over time.

Turning now to the drawing figures in detail, which drawing figures are examples of the dosage forms provided by the invention, and which examples are not to be construed as limiting the invention, one example of a dosage form is illustrated in FIG. 1, and designated by the numeral 10. In FIG. 1, dosage form 10 comprises a body 11 comprising a non-toxic wall 12 that surrounds and encloses an internal compartment, not seen in FIG. 1. Dosage form 10 comprises at least one exit port 13 that connects the interior of dosage form 10 with the exterior of dosage form 10.

Figure 2:
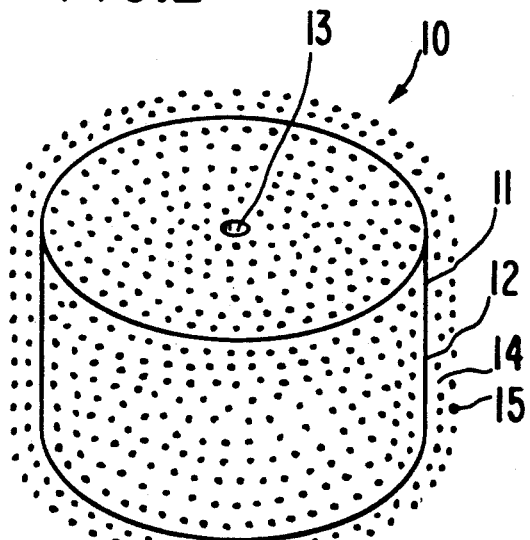
FIG. 2 is a view of a dosage form provided by the invention comprising an exterior dosage amount of drug for an initial burst dose of a drug to the gastrointestinal tract consisting of the stomach and the small intestine.

FIG. 2 illustrates dosage form 10 of FIG. 1 comprising body 11 consisting of wall 12 and exit port 13, and an additional exterior quick-release coat 14. Coat 14 comprises a dose amount of drug 15 for supplying an initial dose of drug to the environment of use, the gastrointestinal tract of a warm-blooded animal comprising the stomach and the intestine. Exterior coat 14 comprises about 0.1 weight percent (wt %) to 99.9 wt % of a drug 15 and from 0.1 wt % to 99.9 wt % of a pharmaceutically acceptable quick-release coat for supplying instant drug 15 therapy to a patient in need of drug 15. In a presently preferred manufacture, the quick-release coat 14 comprising drug 15 comprises from 7.5 to 85 wt % of drug 15 and 92.5 to 15 wt % of a quick-release coat 14 carrier. Drug 15, expressed as mg present in instant coat 14, generally is 10 mg to 150 mg, and more preferably 100 mg to 150 mg, of drug 15 for quick release therapy. Coat 14 is a carrier for coating drug 15 onto the exterior surface of wall 12. In a fluid environment of use, the coat 14 releases drug 15 for providing an initial dose of drug 15 to the stomach and the small intestine. The quick-release coat 14 releases drug 15 in from greater than one second up to one hour, and in a presently preferred quick-release dose of from two minutes, up to thirty minutes. Presently preferred quick-release coat 14 is made from hydrophilic polymers, that are in a presently preferred embodiment a member selected from the group consisting of a hexahydric alcohol, sorbitol, mannitol, acacia, a hydroxycellulose, hydroxymethylcellulose, hydroxyethylcellulose, hydroxypropylcellulose, hydroxyisopropylcellulose, hydroxypropylmethylcellulose, hydroxypropylethylcellulose, and microcrystalline cellulose. Representative coats are discussed in U.S. Pat. No. 4,948,592.

Figure 3:
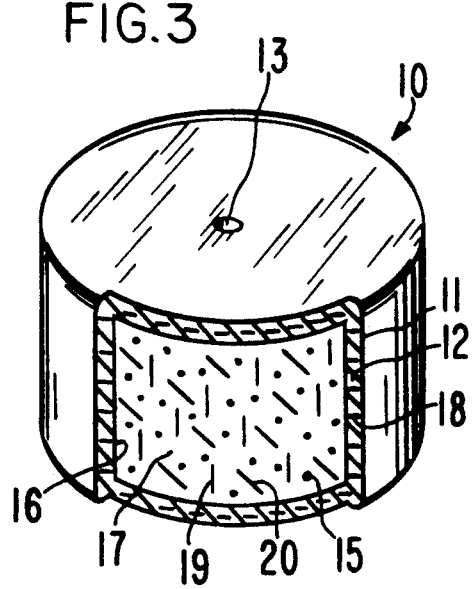
FIG. 3 is an opened view of a dosage form provided by the invention, which dosage form is manufactured as an osmotic device designed for oral administration for delivering a drug in a period up to eight hours; and, FIG. 4 is an opened view of a dosage form provided by the invention, which opened view depicts the structure of the dosage form.

FIG. 3 is a view of dosage form 10, seen in opened section with wall 12 sectioned at 16 for illustrating the structure and composition of dosage form 10. In FIG. 3, dosage form 10 is manufactured as an osmotic device, comprising body 11, wall 12 and exit port 13. Wall 12 surrounds and forms an internal compartment 17 connected through at least one exit port 13 to the exterior of dosage form 10. Wall 12 of dosage form 10 comprises totally, or in at least a part, wall-forming composition that is permeable to the passage of an exterior fluid present in the environment of use, and it is substantially impermeable to the passage of drug 15 and other ingredients present in compartment 17. Wall 12, is semipermeable, and it comprises a polymeric composition that is inert and maintains its physical and chemical integrity during the life-time of dosage form 10. The phrase, "maintains its physical and chemical integrity", denotes wall 12, as exemplified by the wall-forming materials set forth hereafter, does not lose its structure and it does not change chemically during the dispensing life of dosage form 10. Representative materials for forming wall 12 comprise a selectively semipermeable polymer selected from the group consisting of a cellulose ether, cellulose ester, cellulose esterether, cellulose acylate, cellulose diacylate, cellulose triacylate, cellulose acetate, cellulose diacetate and cellulose triacetate. Representative of semipermeable polymers for manufacturing, wall 12 comprises cellulose acetate comprising an acetyl content of 25 to 35%, cellulose acetate comprising an acetyl content of 36 to 4%, an cellulose acetate comprising an acetyl content of 41 to 45%. The semipermeable polymers are disclosed in U.S. Pat. No. 4,948,592.

Dosage form 10, as seen in FIG. 3, comprises an improvement in the design and development of dosage form 10. The improvement in the design and development of dosage form 10. The improvement comprises a high fluid-flux agent 18 represented by dashes in wall 12. The term "fluid" as used for the purpose of this invention includes aqueous and biological fluids. The fluid-flux agent 18 increases the volume of fluid imbibed into compartment 17 for enabling dosage form 10 to dispense substantially all of drug 15 from compartment 17 in from twenty minutes to eight hours. The improvement in wall 12 comprises the proviso that the fluid-flux of agent 18 is greater than the semipermeable polymeric composition comprising wall 12. The fluid-flux of agent 18 increases the volume of fluid passage into compartment 17 from 20 to 45 times greater than the fluid passage through a semipermeable polymeric composition. Wall 12, for the purpose of this invention, comprises 40 to 55% of fluid-flux agent 18, more preferably 40 to 50%, for effecting drug 15 delivery program of the invention. The fluid-flux of agent 18 of an external fluid, which is the fluid vapor transmission, can be determined by using the procedure presented in $Diffusion\ In\ Polymers$, by Crank and Park, pages 1 to 39 and 259 to 313, (1968) published by Academic Press, N.Y., and then expressing the results as the fluid vapor transmission rate in milliliters per square centimeter of agent 18. Representative of fluid-flux agent 18 comprises a member selected from the group consisting of polyvinylpyrrolidone, possessing a 10,000 to 1,750,000 molecular weight; a polyvinyl pyrrolidone comprising a 38,000 to 45,000 molecular weight; a copolymer of vinylpyrrolidone and vinyl acetate possessing a 10,000 to 500,000 molecular weight; a copolymer vinylpyrrolidone and vinyl propionate possessing a 10,000 to 500,000 molecular weight; a copolymer of vinylpyrrolidone and vinyl butyrate possessing a 10,000 to 500,000 molecular weight; a copolymer of vinylpyrrolidone and a vinyl ester selected from the group consisting of vinyl caproate, vinyl octanoate, vinyl laurate, vinyl palmitate, vinyl stearate, vinyl isostearate and vinyl behenate, possessing a 10,000 to 500,000 molecular weight; a colloid; a water-soluble polymer selected from the group consisting of an alginate, acacia, carrageenan, guar gum, karaya gum, gum locust bean, tragacanth and xanthan gum; polymeric anhydroglucose substituted with at least one of a member selected from the group consisting of a methoxy group, an ethoxy group, a hydroxyethoxy group, a hydroxypropoxy group, a hydroxypropyl-methoxy group and a carboxymethoxy group. The high concentration of fluid-flux agent 18 in wall 12 substantially overcomes the start-up time needed for imbibing an external fluid through wall 12 for dosage form to hydrodynamically deliver a drug 15 in up to eight hours, and more preferably, in thirty minutes to 6 hours. For the purpose of the present invention, the fluid-flux agent 18 comprises a 10,000 to 1,750,000 molecular weight. Polymeric polymers 1- useful for the purpose of the invention are disclosed in $Handbook\ of\ Water-Soluble\ Gums\ and\ Resins$, by Davidson, (1980) published by the McGraw-Hill Book Co., and in $Pharmaceutical\ Dosage\ Forms$, by Lieberman et al, Vol. 2, (1989) published by Marcel Dekker, Inc.

Wall 12 in a presently preferred manufacture comprises 0 to 5% of a plasticizer to enhance the operability and flexibility of wall 12. The plasticizer comprises a member selected from the group consisting of an adipate, azelate, benzoate, citrate, stearate, isoebucate, sebacate, triethyl citrate, tri-n-butyl citrate, acetyl tri-n-butyl citrate, acetyl tri-2-ethylhexyl citrate, 1,2,3-propanetriol triacetate, citric acid esters, polyethylene glycol 400 and polyethylene glycol 3350. Plasticizers are known in $Encyclopedia\ of\ Polymer\ Sciences\ and\ Technology$, Vol. 10, (1969), published by John Wiley & Sons.

The expression "drug 15" as used herein, denotes a drug that can be delivered from the dosage form 10 to a patient in need of therapy to produce a local or a systemic therapeutic effect. The drug 15 that can be delivered includes inorganic and organic drugs selected from the group consisting of central nervous system drugs, depressants, hypnotics, sedatives, psychic energizers, tranquilizers, anticonvulsants, muscle relaxants, anti-parkinson drugs, anti-inflammatories, anesthetics, muscle contractants, antimicrobials, hormonal drugs, contraceptives, diuretics, sympathomimeters, antiparasitics, neoplastics, hypoglycemics, antihistamine drugs, cardiovascular drugs, calcium channel inhibitors, angiotensin converting enzyme inhibitors, anti-ulcer drugs, and nonsteroidal anti-inflammatory drugs.

Representative of drugs 15 that can be contained in compartment 17 and delivered through exit port 13 comprise histamine $H_1$ receptor antagonists, and histamine $H_2$ receptor antagonists, comprising a member selected from the group consisting of cimetidine, ranitidine, famotidine, nizatidine, bifentidine, erbrotidine, nifentidine, and roxatidine; proton pump inhibitors consisting of omeprazole and lansoprazole; nonsteroidal anti-inflammatory analgesics comprising a member selected from the group consisting of benoxaprofen, carprofen, flurbiprofen, fenoprofen, fenbufen, ibuprofen, indoprofen, ketoprofen, naproxen, miroprofen, oxaprozin, pranoprofen, pirprofen, suprofen, traporfenic, fluprofen, alminoprofen, bucloxic, alcofenac, acematacin, aspirin, diclofenac, indomethacin, ibufenac, isoxepac, furofenac, fentiazac, clidanac, oxpinac, sulindac, tolmetin, zomepirac, zidometacin, and mefenamic; angiotensin-converting inhibitors including quinapril, indolapril, olindapril, rentiapril, spirapril, cilazaprilat, lisinopril, imidapril, benazeprilat, cilazapril, alacipril, captopril, delapril, fosinopril, libenzapril, pentopril, perindopril, altiopril, quinaprilat, ramipril, spiraprilat, teprotide, zofenopril, enalapril, benazepril, enalaprilat, 1-sarcosine-8-isoleucine angiotensin II, antipain and cilastatin; and calcium channel blockers, including amrinone, bencyclane, bepridil, diltiazem, felodipine, fendiline, flunarizine, nicardipine, amlodipine, isradipine, nifedipine, nimodipine, nisoldipine, nitredipine, perhexiline, nilvadipine, prenylamine, verapamil, nitredipine, amlodipine, cinnarizine, fendiline, gallopamil, belfosdil, fostedil, arylakylamine calcium channel blocker, dihydropyridine calcium channel blocker, and piperazine calcium channel blocker. The drugs are known in

*USAN and the USP Dictionary of Drug Names*, 1990, published by United States Pharmacopeial Convention, Inc.; *Medical Subject Headings*, 1991, published by U.S. Department of Health and Human Services; and, Pharmaceutical Services, Remington, 18th Ed., 1990, published by Mack Publishing Co.

Drug 15 can be in various forms, such as charged and uncharged molecules, molecular complexes, pharmaceutically acceptable salts including inorganic, organic, hydrochloride, hydrobiomide, sulfate, laurate, palmitate, phosphate, nitrate, borate, acetate, maleate, tartrate, oleate and salicylate. For acidic drugs, salts of metals, amines or organic cations, for example, quaternary ammonium can be used for forming a dispensable drug. Derivatives of drugs such as esters, ethers and amides can be used. A drug that is water insoluble can be used in a form that is water soluble derivative thereof to serve as a solute, and on its release from the dosage form, is converted by enzymes, hydrolyzed by body pH or other metabolic processes to the original drug active form. The amount of drug in a dosage form generally is from 100 ng to 1500 mg. The amount of drug in a dosage form for individual dosage forms, is for example, 1 mg, 5 mg, 25 mg, 50 mg, 100 mg, 250 mg, 500 mg, 750 mg, 1000 mg, and 1500 mg. The dosage form can be administered once, twice, or thrice daily, one at a time, or two at a time.

Internal compartment 17 additionally contains a composition forming carrier 19 that imbibes an external fluid into compartment 17 for developing an osmotic pressure for pumping drug 15 through exit port 13 from dosage form 10. The carrier 19, represented by vertical dashes 19, also enhances the solubility of drug 15 in fluid imbibed into the compartment 17 to aid in delivering drug 15 from dosage form 10. Representatives of carrier 19 comprise polyvinyl ethers, polyvinyl alcohol, polyvinylpyrrolidone of 10,000 to 450,000 molecular weight, gelatin, polyethylene glycol having a 3,000 to 20,000 molecular weight, sodium alginate, sodium cellulose sulfate, sodium carboxymethylcellulose, hydroxypropylmethylcellulose and polyethylene oxide having a 10,000 to 300,000 molecular weight. The amount of carrier 19 present in compartment 17 is from 0.5 to 15 weight percent. Compartment 17 further contains 0 to 7.5 weight percent of a lubricant 20, represented by slant lines 20. Examples of lubricant 20 include metal stearates such as magnesium stearate, calcium stearate and zinc stearate, and stearic acid. The weight of all ingredients in compartment 17 is equal to 100 weight percent.

Figure 4:
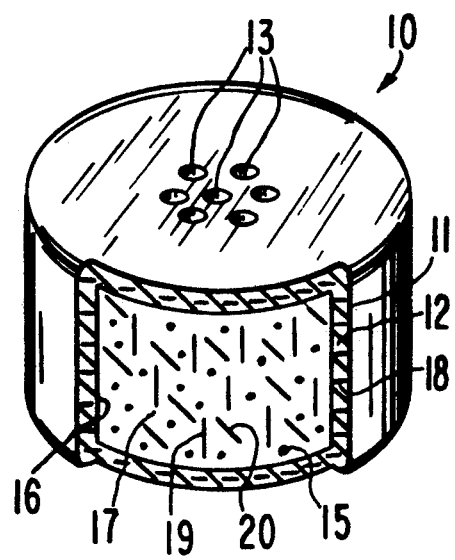

FIG. 4 illustrates another embodiment provided by the invention. In FIG. 4, dosage form 10 comprises body 11, and wall 12 surrounds and defines a compartment 17, which compartment comprises drug 15, carrier 19 and lubricant 20. In FIG. 4, dosage form 10 comprises at least one exit port 13, and in FIG. 4, dosage form 10 comprises a multiplicity of exit ports 13 on both faces or sides of wall 12. The expression, "exit port 13", as used herein comprises means and methods suitable for the metered release of drug 15 from compartment 17 of dosage from 10. The exit port 13 includes at least one passageway, aperture, orifice, bore, pore, porous element through which drug 15 can migrate, hollow fiber, capillary tube, porous overlay, porous insert, laser orifice, mechanical orifice and pressed orifice. The expression includes also a material that erodes, or is leached from wall 12 in the fluid environment of use to produce at least one passageway in dosage form 10. Representative materials suitable for forming at least one passageway, or a multiplicity of passageways, including an erodible poly(glycolic) acid or poly(lactic) acid in wall 12, a gelatinous filament, poly(vinyl alcohol), a leachable material such as a fluid removable pore-forming polysaccharide, salt or oxide. A passageway, or a plurality of passageways can be formed by leaching a material, such as sorbitol from wall 12. The exit port can have any shape such as round, triangular, square, elliptical, and the like, for assisting in the metered release of drug 15 from dosage from 10. Dosage form 10 can be construed with one or more exit port in space apart relations, or more than a single surface of dosage form 10. Exit ports and equipment for forming exit ports are disclosed in U.S. Pat. Nos. 3,845,770; 3,916,899; 4,063,064 and 4,088,864. Exit ports formed by leaching are disclosed in U.S. Pat. Nos. 4,200,098 and 4,285,987.

Dosage form 10 of this invention is manufactured by standard manufacturing techniques. For example, in one manufacture, compartment 17 comprising drug 15 and other dispensing ingredients are formulated by a wet granulation technique or a dry blend technique. The wet granulation technique uses solvent such as ethanol, isopropyl alcohol or water, and cosolvents such as isopropyl alcohol-methylene dichloride 80/20 v/v (volume/volume), cosolvent acetone-ethanol, cosolvent acetone-water, or cosolvent ethanol-methylene dichloride, as granulating fluid. In one manufacture, the ingredients forming compartment 17 comprising drug 15 are pre-sieved through a 40 mesh screen, then wetted with, for example, ethanol or water. The damp ingredients next are passed through a 16 or 20 mesh screen forming granules which are then dried in the open air on trays. After drying, the granules are passed through a 20 mesh screen.

The final core formulation comprising the drug 15 for the compartment 17 is effected by fluid bed granulation. The drug is passed through a 20 mesh screen or through an 8 mesh screen. The sized drug is added to a granulator column. Next, polyvinylpyrrolidone having a 360,000 molecular weight is added to distilled water at a concentration of between 5 and 15% solids. Distilled water is sprayed onto the fluidized bed of drug. The binder solution is sprayed onto the wetted drug immediately following the water. The mixing vessel is rinsed with water and this rinse is then sprayed onto the drug granulation in the column. The granulation is removed and passed through a 20 mesh screen. Next, a lubricant is added and the materials blended into a homogenous blend.

In another manufacture, the ingredients forming the compartment are individually passed through a screen and then thoroughly blended in a mixer. Next, the polymeric carrier is dissolved in a portion of granulation fluid, and a solvent added thereto. Then, the polymeric carrier solution is added slowly to the blend with continual mixing in the blender. The granulation fluid is added until a wet blend is achieved, generally about 400 cc of granulation fluid per kilogram of blend. The wet mass blend is then forced through a 20 mesh screen onto oven trays, and dried for 18 to 24 hours at 50° C. The dried granules are then sized with a 20 mesh screen. Next, a lubricant, passed through an 80 mesh screen, is added to the dry granules. The granulation is placed into a V-blender for 5 to 15 minutes.

In another process, the drug cimetidine and polyvinylpyrrolidone are added to a fluid bed granulator and are dry blended. Next, polyvinylpyrrolidone dissolved in a granulation fluid is slowly sprayed onto the dry blend with continued mixing in the granulator. Next, the granules are dried in the granulator. Then, magnesium stearate is added to the dry granular blend.

In any of the above processes, the composition forming the blend is tabletted using a high speed tablet press. The dosage form is tabletted under a pressure of two tons using a 9/32 inch (7.15 mm) round, standard concave punch or using a ⅜ inch (9.52 mm) round, standard concave punch or a 7/10 inch (17.8 mm) oval punch, or a ¾ inch (19.06 mm) capsule-shaped punch.

Wall 12 of dosage form 10 and exterior coat 14 can be formed using the air suspension procedure. This procedure consists in suspending and tumbling the pressed compartment forming composition in a current of air and a wall-forming composition, or a coat forming composition, until in either operation a wall-forming composition, or the exterior coat is applied to the dosage form. The air suspension procedure is known for independently forming a wall or a coat of a dosage form. The air suspension procedure is described in U.S. Pat. Nos. 2,799,241; and 4,801,461; in *J. Am. Pharm. Assoc.*, Vol. 48, pp. 451 to 459, 1959; and, *J. Am. Pharm. Assoc.*, Vol. 49, pp. 82 to 84, 1960. Dosage forms also can be coated with wall-forming compositions with a Wurster ® air suspension coater using a methylene dichloride-methanol cosolvent, 80/20 wt/wt (weight/weight), using a methylene dichloride-methanol cosolvent, 87/13 wt/wt, also can be used for applying the wall or the coat. Other wall and laminating techniques such as pan coating can be used for manufacturing the dosage form. In the pan coating system, wall-forming or coat forming compositions are deposited by successive spraying of the compositions on the drug accompanied by tumbling in a rotating pan. A pan coater, in another embodiment, can be used to produce a thicker wall or a thicker coat. A larger volume of a solvent or a cosolvent, in another process, can be used to produce a thinner wall or a thinner coat. Finally, the wall or exterior coated dosage forms are dried in a forced air oven at 50° C., 50% RH (relative humidity), after drilling the exit port, for one to seven days to free the dosage form of solvent. Generally, the wall formed by these techniques will have a 2 to 20 mil (0.05 to 0.508 mm) thickness, with a presently preferred thickness of 4 to 10 mils (0.101 to 0.254 mm). The exterior coat generally will have a thickness of 0.3 to 8.5 mils (0.0067 to 0.216 mm).

Exemplary solvents suitable for manufacturing the wall or the coat include inert inorganic or organic solvents, that do not adversely harm the wall, the coat and the final dosage form. The solvents broadly include a number selected from the group consisting of alcohols, ketones, esters, ethers, aliphatic hydrocarbons, halogenated solvents, cycloaliphatic solvents, aromatic, heterocyclic, aqueous solvents, and mixtures thereof.

DETAILED DESCRIPTION OF EXAMPLES

The following examples are merely illustrative of the present invention, and they should not be considered as limiting the scope of the invention in any way, as these examples and other equivalents thereof will become apparent to those versed in the art in the light of the present disclosure, the drawings and the accompanying claims.

EXAMPLE 1

A dosage form for the administration of ranitidine hydrochloride, a histamine $H_2$ receptor antagonist for inhibiting both daytime and nocturnal basal gastric acid secretion, including gastric acid secretion stimulation is prepared as follows: first, 168 mg of ranitidine hydrochloride, 2.5 mg of hydroxypropylmethylcellulose, 12.2 mg of microcrystalline cellulose, 15.7 mg of polyvinylpyrrolidone having a 40,000 molecular weight, and 2.6 mg of magnesium stearate, are dry blended into a homogenous blend. Next, the dry blend is wetted with 350 ml of anhydrous ethanol, followed by drying in an oven for 14 to 17 hours at 30° C. The dry granules then are passed through a 20 mesh screen, and compressed under 2 tons to yield a solid core.

Next, the solid core is surrounded with a semipermeable wall-forming composition. The wall-forming composition comprises 56 wt % cellulose acetate comprising an acetyl content of 39.8%, 45 wt % polyvinylpyrrolidone having a 42,000 molecular weight and 2% tripropyl citrate are dissolved in a cosolvent comprising methylene chloride-methanol, 85-15 wt %, to obtain 5% solids. The wall-forming composition is coated around the core in an Aeromatic ® air suspension coater. The core is surrounded with a wall-forming composition by applying a 4.2 mg wall per coat.

Finally, a passageway, 0.35 mm diameter, is drilled through the semipermeable wall for connecting the interior of the dosage form with the exterior of the dosage form. The dosage form is dried in a forced air oven at 50° C. for 40 hours to remove all solvents. The dosage form is sized and shaped for oral admittance into the gastrointestinal tract of a human for delivering dose ranitidine in 6 hours for the desired therapy.

EXAMPLE 2

The procedure of Example 1 is repeated in this example with all manufacturing steps as previously set forth, except that in this example, the wall comprising the semipermeable composition is coated on the exterior surface with an instant release ranitidine coat. The instant coat is applied to the exterior surface of the wall from a composition comprising 10 mg of ranitidine hydrochloride 25 mg of mannitol and 25 mg of hydroxypropylcellulose dissolved in distilled water and dried to yield and instant release coat. A 0.30 mm passageway is drilled through the outermost coat and the wall for releasing the ranitidine from the dosage form. The dosage form provided by this example effects instant release ranitidine therapy for the exterior coat followed by ranitidine therapy form inside the dosage form for up to 6 hours.

EXAMPLE 3

The procedures of Examples 1 and 2 are followed to produce an oral dosage form comprising 20 mg of famotidine, a competitive inhibitor of histamine $H_2$ receptors for maintenance therapy.

EXAMPLE 4

A dosage form is manufactured according to the above examples, for administering omeprazole. The dosage form comprises an enteric coat for restricting drug delivery in the stomach and for providing drug release in the small intestine in a period up to 4 hours. The dosage form comprises 40 mg of omeprazole in the dosage form for suppressing gastric acid secretion by specific inhibition of $H^+/K^+$ ATPase enzyme system at the secretory surface of gastric parietal cell.

EXAMPLE 5

A dosage form for administering cimetidine to a patient in need of cimetidine therapy is prepared as follows: first 70 kg of cimetidine hydrochloride is passed through a sizing screen and then added to the bowl of a fluid bed granulator. Next, 2.93 kg of polyvinylpyrrolidone having a 360,000 molecular weight is mixed with purified water and the resulting fluid is metered into the granulator in small volumes to dampen the cimetidine hydrochloride. Then, the resulting granulation is dried and passed through a 20 mesh screen. Next, 0.357 kg of magnesium stearate is added to the granules and blended with the granules. The granules are fed to a compression press and pressed into cores under 2 tons of pressure. The cores consisted of 89.6% cimetidine hydrochloride, 4.0 wt % polyvinylpyrrolidone, 0.5 wt % magnesium stearate, and 5.9 wt % bound water, to the cimetidine hydrochloride monohydrate of 306.81 molecular weight.

Next, a wall-forming composition is prepared as follows: 55.0 wt % of cellulose acetate comprising a 39.8% acetyl content is homogeneously blended with 43 wt % polyvinylpyrrolidone comprising a 40,000 average molecular weight is mixed with an acetone-methyl alcohol cosolvent, 80 wt %-20 wt %, comprising 6% solids, and mixing continued until a clear solution results. Next, 2 wt % tri-ethyl citrate is added thereto with continual mixing to obtain a clear wall-forming solution. Next, the compressed cores are placed in a coater, and the cores coated with the wall-forming composition. A wall comprising 40.7 mg of cellulose acetate, 31.8 mg of polyvinylpyrrolidone and 1.5 mg of tri-ethyl citrate is applied to each core. The wall composition weighed 74.0 mg. Then, the coated cores are removed from the coater and two delivery orifices, one on each side of the dosage form, is drilled through each surface. Each orifice is 10 mils (0.254 mm) in diameter. The drilled dosage forms are placed on trays in an oven to remove the cosolvent, to provide the dosage form. The dosage form delivers the cimetidine hydrochloride in six hours.

EXAMPLE 6

The procedure of Example 5 is followed in this procedure. In this examples, an exterior quick release cimetidine hydrochloride coat is applied to the exterior surface of the dosage form. The exterior coat is applied from a coat comprising 2,380 g of cimetidine hydrochloride, 680 g of mannitol, 340 g of acacia and 13,600 g of purified water. The coat is applied by mixing the water, cimetidine hydrochloride, mannitol and acacia into a clear solution with added heat. The coat is applied from an air suspension coater or pan coater to yield an exterior coat comprising 70 wt % cimetidine hydrochloride, 20 wt % mannitol and 10 wt % acacia. The dosage form delivers the external dose of cimetidine hydrochloride in 20 minutes.

EXAMPLE 7

An embodiment of the invention pertains to the use of the dosage form in a method for treating a gastrointestinal ulcer wherein the method comprises: (1) admitting the dosage form orally into a patient in need of anti-ulcer therapy, the dosage form comprising: (a) a semipermeable wall permeable to fluid and comprising a high concentration of means for increasing fluid flux into the dosage form, which wall surrounds; (b) a compartment; (c) a dose amount of an anti-ulcer drug in the compartment and (d) an exit port in the wall for delivering the anti-ulcer drug from the dosage form; (2) imbibing fluid through the wall and (3) passing fluid through the means for increasing fluid passage into the dosage form; and, (4) delivering the drug by the combined operation of (2) and (3) in up to 8 hours to the patient for treating the ulcer. The use of the dosage form in the method also comprises administering a histamine receptor antagonist drug and a hydrogen ion inhibitor drug to the patient for management and the control of gastric secretion.

In summary, it will be appreciated the present invention contributes to the drug dispensing art by providing an unobvious and unique dosage form that possesses a practical utility, and can administer a drug at a metered release rate up to eight hours for preselected therapy. While the invention has been described and pointed out in detail with reference to operative embodiments thereof, it will be understood by those skilled in the art that various changes, modifications, substitutions and omissions can be made without departing from the spirit of the invention. It is intended, therefore, that the invention embraces those equivalents within the scope of the claims which follow.

We claim:

1. An improvement in a method for administering a drug to a patient in need of gastrointestinal therapy, wherein the method comprises:
   (a) admitting orally into the gastrointestinal tract of the patient a dosage form comprising:
      (1) a semipermeable wall permeable to fluid, which wall surrounds:
      (2) a compartment;
      (3) means in the wall for increasing fluid-passage into the dosage form, said means comprising 40 to 55% of the wall;
      (4) a drug in the compartment for gastrointestinal therapy;
      (5) a passageway in the wall for delivering the drug from the dosage form;
   (b) letting gastrointestinal fluid enter the dosage form by (1) passing fluid through the semipermeable wall and (3) passing fluid through the means; and wherein the improvement comprises:
   (c) delivering the drug from the compartment by the combined operations of (1) and (3) in up to 8 hours to the gastrointestinal tract for the gastrointestinal therapy.

2. The improvement in a method for administering the drug to the patient in need of gastrointestinal therapy according to claim 1, wherein the method comprises administering a drug possessing histamine receptor antagonist therapy.

3. The improvement in a method for administering the drug to the patient in need of gastrointestinal therapy according to claim 1, wherein the method comprises administering a drug possessing hydrogen ion suppression therapy.

4. The improvement in a method for administering the drug to the patient in need of gastrointestinal therapy according to claim 1, wherein the method comprises administering a drug possessing anti-ulcer therapy.

5. The improvement in a method for administering the drug to the patient in need of gastrointestinal therapy according to claim 1, wherein an instant release coat comprising a gastrointestinal drug is present on the semipermeable wall.

6. The improvement in a method for administering the drug to the patient in need of gastrointestinal therapy according to claim 1, wherein the drug is cimetidine.

7. An improvement in a dosage form for delivering a drug, wherein the dosage form comprises:
   (1) a semipermeable wall permeable to the passage of fluid, which wall surrounds:
   (2) a compartment;
   (3) a drug in the compartment;
   (4) a passageway in the wall for delivering the drug form the dosage form; and wherein the improvement comprises:
   (5) means in the wall for increasing fluid-flux into the dosage form, said means comprising 40 to 55% of the wall; and which dosage form;
   (6) delivers the drug from the compartment by the combined operations of (1) the semipermeable wall permitting fluid to pass through the wall into the compartment and by (5) the means in the wall permitting fluid to pass into the compartment, whereby the drug in the compartment is delivered in up to 8 hours from the dosage form.

8. The improvement in the dosage form for delivering the drug according to claim 7, wherein the dosage form comprises 100 ng to 1500 mg of drug.

9. The improvement in the dosage form for delivering the drug according to claim 7, wherein the dosage form comprises 100 ng to 1500 mg of cimetidine.

10. The improvement in the dosage form for delivering the drug according to claim 7, wherein the dosage form comprises 100 ng to 1500 mg of a drug selected from the group consisting of ranitidine, famotidine, nizatidine, bifentidine, erbrotidine, nifentidine, roxatidine, omeprazole, and lansoprazole.

11. An improvement in a dosage form for delivering a drug, wherein the dosage form comprises:
   (1) a semipermeable wall permeable to the passage of fluid that surrounds;
   (2) a compartment;
   (3) 100 ng to 1550 mg of a drug comprising a member selected from the group consisting of quinapril, indolapril, olindapril, rentiapril, spirapril, cilazaprilat, lisinopril, imidapril, benazeprilat, cilazapril, alacepril, captopril, delapril, fosinopril, libenzapril, pentopril, perindopril, altiopril, quinaprilat, ramipril, spiraprilat, teprotide, zofenopril, enalapril, benazepril, enalaprilat, antipain and cilastatin;
   (4) an exit port in the wall for delivering the drug from the dosage form, and wherein the improvement comprises:
   (5) means in the wall for increasing fluid-passage into the dosage form, said means comprising 40 to 55% of the wall; and which dosage form;
   (6) delivers the drug from the compartment by the combined operations of (1) letting fluid pass through the semipermeable wall into the compartment and by (2) the means in the wall permitting an increase of fluid passage into the compartment, whereby the drug is delivered in up to 8 hours form the dosage form.

12. An improvement in a dosage form for delivering a drug, wherein the dosage form comprises:
   (1) a semipermeable wall permeable to the passage of fluid that surrounds;
   (2) a compartment;
   (3) 100 ng to 1500 mg of a drug in the compartment, said drug a member selected from the group consisting of amrinone, bepridil, diltiazem, felodipine, fendiline, flunarizine, nicardipine, isradipine, nifedipine, nimodipine, nisoldipine, perhexiline, amlodipine, nilvadipine, prenylamine, verapamil, nitredipine, cinnarizine, gallopamil, belfosdil, and fostedil;
   (4) an exit port in the wall for delivering the drug from the dosage form, and wherein the improvement comprises:
   (5) chemical means in the wall for increasing fluid-passage into the compartment, said means comprising 40 to 55% of the wall; and which dosage form;
   (6) delivers the drug (3) by the combined operation of (1) the semipermeable wall letting fluid pass through the wall into the compartment and by (5) the means in the wall permitting an increase in fluid passage into the compartment in up to 8 hours from the dosage form.

13. An improvement in a dosage form for orally delivering an anti-ulcer drug to the stomach and the small intestine to a patient, wherein the dosage form comprises:
   (1) a semipermeable wall permeable to the passage of fluid which wall comprises an exterior surface;
   (2) a dose of an anti-ulcer drug on the exterior surface of the wall;
   (3) a compartment formed by the wall;
   (4) 100 ng to 1500 mg of an anti-ulcer drug in the compartment;
   (5) an exit port in the wall for delivering the drug from the dosage form, and wherein the improvement comprises:
   (6) fluid-flux increasing means in the wall for increasing the volume of fluid into the dosage form, said means comprising 40 to 55% of the wall; and which dosage form;
   (7) delivers the anti-ulcer drug form the exterior wall and delivers the anti-ulcer drug from the compartment by the combined operations of (1) the semipermeable wall letting fluid pass through the wall into the compartment and by (6) the means in the wall increasing fluid flux into the compartment, in up to 8 hours to the stomach and the small intestine.

14. The improvement in a dosage form for orally administering the drug according to claim 13, wherein the anti-ulcer drug in the compartment is a histamine antagonist.

15. The improvement in a dosage form for orally administering the drug according to claim 13, wherein the dosage form comprises multiple exit ports.

16. The improvement in the dosage form for orally administering the drug according to claim 13, wherein the exterior surface comprises 10 mg to 150 mg of anti-ulcer drug.

17. The improvement in the dosage form for orally administering the drug according to claim 13, wherein the small intestine consists of a member selected from the group consisting of the duodenum, the jejunum and the ileum.

18. The improvement in the dosage form for orally administering the drug according to claim 13, wherein the quick release dose is administered in one second to one hour.

19. The improvement in the dosage form for orally administering the drug according to claim 13, wherein the drug is delivered from the compartment in thirty minutes to six hours.

20. A composition comprising: 40 to 60 wt % cellulose acylate, 40 to 55% polyvinylpyrrolidone comprising a 38,000 to 45,000 molecular weight, and 0 to 5 wt % plasticizer, which composition equals 100 wt % and is useful for manufacturing an orally administerable dosage form.

21. The composition according to claim 20, wherein the cellulose acylate is cellulose acetate.

22. A method for delivering a histamine receptor antagonist drug to an animal, wherein the method comprises:
  (a) admitting into the gastrointestinal tract of the animal a dosage form comprising:
    (1) a semipermeable wall permeable to the passage of fluid comprising an exterior surface;
    (2) a dose of a histamine receptor antagonist drug on the exterior surface of the wall;
    (3) a compartment formed by the wall;
    (4) 100 ng to 1,500 mg of a histamine receptor antagonist drug in the compartment;
    (5) an exit port in the wall for delivering the drug from the dosage form;
    (6) fluid-flux increasing means in the wall for increasing the volume of fluid passing into the dosage form;
  (b) imbibing fluid into the dosage form; and,
  (c) delivering the histamine receptor antagonist drug from the exterior surface of the wall and from the compartment in less than 8 hours to the gastrointestinal tract.

23. A method for delivering a calcium influx inhibitor drug that inhibits a transmembrane influx of calcium ions into cardiac muscles and smooth muscles, wherein the method comprises:
  (a) admitting into the gastrointestinal tract of the animal a dosage form comprising:
    (1) a wall comprising an exterior surface;
    (2) a dose of a calcium influx inhibitor drug, in contact with the exterior surface of the wall;
    (3) a compartment defined by the wall;
    (4) fluid-flux increasing means in the wall for increasing the volume of fluid passing through the wall into the dosage form;
    (5) 100 ng to 1,500 mg of a calcium influx inhibitor drug in the dosage form;
    (6) an exit passageway in the wall for delivering the drug from the dosage form;
  (b) imbibing fluid into the dosage form; and,
  (c) delivering the calcium influx inhibitor drug form the dosage form in less than 8 hours to the animal.

24. A method for delivering an angiotensin converting enzyme inhibitor to the gastrointestinal tact of an animal, wherein the method comprises:
  (a) admitting into the gastrointestinal tract of the animal a dosage form comprising:
    (1) a wall comprising an exterior surface;
    (2) a dose of an angiotensin converting enzyme inhibitor in contact with the exterior surface of the wall;
    (3) a compartment defined by the wall;
    (4) fluid-flux increasing means in the wall for increasing the volume of fluid passing into the dosage form;
    (5) 100 ng to 1,500 mg of an angiotensin converting enzyme inhibitor in the compartment;
    (6) a passageway in the wall for delivering the drug from the dosage form;
  (b) imbibing fluid into the dosage form; and,
  (c) delivering 100 ng to 1,500 mg of the angiotensin converting enzyme inhibitor in less than 8 hours form the dosage form to the animal.

* * * * *

UNITED STATES PATENT AND TRADEMARK OFFICE
CERTIFICATE OF CORRECTION

PATENT NO. : 5,178,867

DATED : January 12, 1993

INVENTOR(S) : George V. Guittard, et al

It is certified that error appears in the above-identified patent and that said Letters Patent is hereby corrected as shown below:

Column 14, line 40, "form" should read --from--.

Signed and Sealed this

Seventh Day of December, 1993

Attest:

BRUCE LEHMAN

Attesting Officer    Commissioner of Patents and Trademarks